United States Patent [19]

Regel et al.

[11] 4,243,670
[45] Jan. 6, 1981

[54] α-(4-BIPHENYLYL)-BENZYL-AZOLIUM SALTS AND THEIR USE FOR COMBATING MICRO-ORGANISMS

[75] Inventors: Erik Regel; Wilfried Draber; Karl H. Büchel; Manfred Plempel, all of Wuppertal, Fed. Rep. of Germany

[73] Assignee: Bayer Aktiengesellschaft, Leverkusen, Fed. Rep. of Germany

[21] Appl. No.: 14,783

[22] Filed: Feb. 23, 1979

Related U.S. Application Data

[63] Continuation of Ser. No. 833,630, Sep. 15, 1977, abandoned.

[30] Foreign Application Priority Data

Sep. 28, 1976 [DE] Fed. Rep. of Germany ....... 2643563

[51] Int. Cl.³ ............ A01N 43/26; A01N 43/28; C07D 233/56; C07D 249/08
[52] U.S. Cl. .................. 424/269; 424/54; 424/232; 424/245; 424/273 R; 252/106; 548/262; 548/341; 548/345
[58] Field of Search ............ 260/308 R; 548/345, 548/341, 262; 424/269, 273, 232

[56] References Cited

U.S. PATENT DOCUMENTS

| 3,658,813 | 4/1972 | Godefroi et al. | 548/341 |
|---|---|---|---|
| 3,711,502 | 1/1973 | Büchel et al. | 548/345 |
| 3,836,540 | 9/1974 | Van Der Stelt | 548/345 |
| 3,991,202 | 11/1976 | Janssen et al. | 548/341 |
| 4,118,487 | 10/1978 | Regel et al. | 260/308 R |

FOREIGN PATENT DOCUMENTS 2461406  7/1976  Fed. Rep. of Germany ...... 260/308 R

OTHER PUBLICATIONS

Horsfall, Fungicides and Their Action, (Waltham, Mass., USA, 1945), pp. 136–139.

Primary Examiner—Alton D. Rollins

[57] ABSTRACT

The present invention relates to novel α-(4-biphenylyl)-benzyl-azolium salts of the general formula

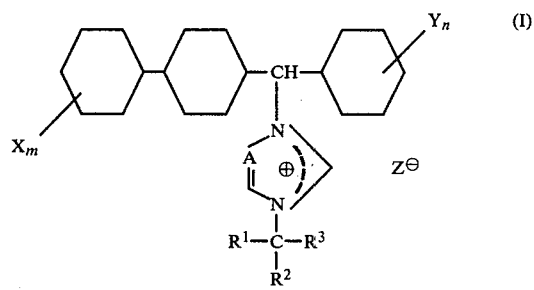

in which
  A represents the CH group or a N atom
  $R^1$ and $R^2$ are identical or different and each represents hydrogen, alkyl or optionally substituted phenyl,
  $R^3$ represents hydrogen, alkyl, or an optionally substituted phenyl, phenylalkyl, phenylcarbonyl or phenylcarbonylalkyl group,
  X represents halogen, alkyl, halogenoalkyl, alkoxy, alkylthio, nitro or cyano,
  Y represents X or optionally substituted phenyl,
  m and n each represents 0 or an integer from 1 to 5 and
  Z represents the anion of an inorganic or organic acid.

The invention also includes processes for the preparation of the compounds and, in addition includes compositions containing the compounds and methods for their use. The compounds of the invention exhibit antimicrobial activity and sporicidal activity.

9 Claims, No Drawings

α-(4-BIPHENYLYL)-BENZYL-AZOLIUM SALTS AND THEIR USE FOR COMBATING MICRO-ORGANISMS

This is a continuation, of application Ser. No. 833,630, filed Sept. 15, 1977, now abandoned.

The present invention relates to new α-(4-biphenylyl)-benzyl-azolium salts, a process for their preparation and their use for combating micro-organisms, especially in the hygiene sector and in the industrial field.

It has already been disclosed that N-tritylimidazoles, especially diphenyl-(2-chlorophenyl-imidazol-1-yl)-methane (clotrimazole, Canesten ®), exhibit a good to very good antimicrobial, especially antimycotic action (compare Belgian Patent Specification 720,801); the same is true of certain azol-1-yl-methanes, such as diphenylyl-phenyl-azol-1-yl-methane (compare German Offenlegungsschrift No. 2,461,406). However, all these azole derivatives have the disadvantage that a long period elapses until their action commences.

According to the present invention there has been provided the following compounds, namely α-(4-biphenylyl)-benzyl-azolium salts of the general formula

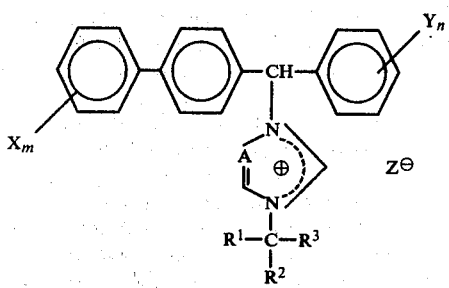

in which
A represents the CH group or a N atom
$R^1$ and $R^2$ are identical or different and each represents hydrogen, alkyl or optionally substituted phenyl,
$R^3$ represents hydrogen, alkyl, or an optionally substituted phenyl, phenylalkyl, phenylcarbonyl or phenylcarbonylalkyl group,
X represents halogen, alkyl, halogenoalkyl, alkoxy, alkylthio, nitro or cyano,
Y represents X or optionally substituted phenyl,
m and n each represents 0 or an integer from 1 to 5 and
Z represents the anion of an inorganic or organic acid.

The compounds of the invention exhibit good antimicrobial properties with a simultaneous sporicidal activity.

Further, it has been found that the new α-(4-biphenylyl)-benzyl-azolium salts of the formula (I) are obtained when 1-(α-biphenylyl-benzyl)-azoles of the formula

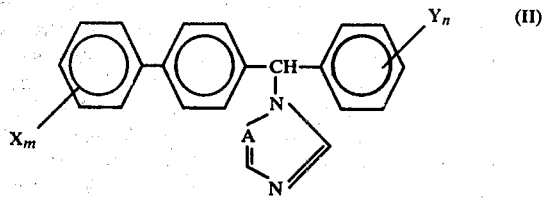

in which
A, X, Y, m and n have the abovementioned meaning, are reacted with halides of the formula

in which
$R^1$, $R^2$ and $R^3$ have the abovementioned meaning and Hal represents halogen, in the presence of a diluent and, if desired, the halide in the resulting azolium halides is replaced by another anion in a manner which is in itself known.

In some cases it is advantageous to employ, in place of the halides of the formula (III), corresponding reactive esters which are obtained by reacting the corresponding alcohols with the corresponding acids.

Surprisingly, the good antimicrobial action of the α-(4-biphenylyl)-benzyl-azolium salts according to the invention starts much more rapidly than is the case with the N-tritylimidazoles known from the state of the art, and with the azol-1-yl-methanes. In addition, the active compounds according to the invention surprisingly also show an almost complete sporicidal action on dermatophyte spores and mould spores. The active compounds according to the invention are therefore useful in pharmacy.

If 1-[α-(4-biphenyl)-benzyl]-imidazole and α-(4-biphenylyl)-benzyl chloride are used as starting materials, the course of the reaction can be presented by the following equation:

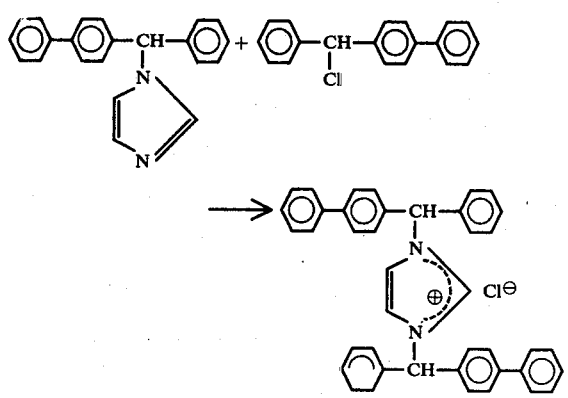

The formula (II) provides a general definition of the 1-[α-(4-biphenylyl)-benzyl]-azoles used as starting materials. In this formula, X preferably represents halogen, especially chlorine and bromine; alkyl with 1 to 6, especially with up to 4, carbon atoms, examples being methyl, ethyl isopropyl and tert.-butyl; halogenoalkyl with 1 to 4 carbon atoms and up to 5 halogen atoms, especially with 1 to 2 carbon atoms and up to three identical or different halogen atoms, the halogens being fluorine and chlorine, and trifluoromethyl being an example; and also, preferably, alkoxy and alkylthio with 1 to 4 carbon atoms, such as, for example, methoxy, ethoxy, methylthio and ethylthio; as well as nitro or cyano, Y preferably represents the radicals which have already been mentioned preferentially in connection with X, and also phenyl optionally substituted by X.

The indices m and n each preferably represents 0 or an integer from 1 to 3, and A is as defined previously.

The 1-[α-(4-biphenylyl)-benzyl]-azoles of the formula (II) to be used, according to the invention, as starting materials, are known (compare German Offenlegungsschrift No. 2,461,406) or can be prepared in accordance with the processes indicated there. They are obtained, for example, when the corresponding 1-[α-(4-biphenylyl)-benzyl]-carbinols are reacted with thionyl-bis-azoles in the presence of a solvent, for example acetonitrile, at temperatures between about 0° and 100° C. or when, for example, the corresponding 1-[α-(4-biphenylyl)-benzyl] halides are reacted with azoles, if appropriate in the presence of an acid-binding agent, for example an excess of azole, and, if appropriate, in the presence of a solvent, for example acetonitrile, at temperatures between about 80° and 120° C. (compare also the preparation examples).

The following may be mentioned as examples of the 1-[α-(4-biphenylyl)-benzyl]-azoles of the formula (II), to be used, according to the invention, as starting materials: 1-[α-(4-biphenylyl)-benzyl]-imidazole, 1-[α-(4-biphenylyl)-(2-chlorobenzyl)]-imidazole, 1-[α-(4-biphenylyl-(3-chlorobenzyl)]-imidazole, 1-[α-(4-biphenylyl)-(4-chlorobenzyl)]-imidazole, 1-[α-(4-biphenylyl)-(4-bromobenzyl)]-imidazole, 1-[α-(4-biphenylyl)-(3-methylbenzyl)]-imidazole, 1-[α-(4-biphenylyl)-(4-tert.-butylbenzyl)]-imidazole, 1-[α-(4-(4'-chlorobiphenylyl))-benzyl]-imidazole, 1-[α-(4-(4'-chlorobiphenylyl))-(2-chlorobenzyl)]-imidazole, 1-[α-(4-(2',4',6'-trichlorobiphenylyl))-benzyl]-imidazole, 1-[α-(4-(3'-methylbiphenylyl))-benzyl]-imidazole, 1-[α-(4-(3'-ethylbiphenylyl))-benzyl]-imidazole, 1-[α-(4-biphenylyl)-(2,4-dichlorobenzyl)]-imidazole, 1-[α-(4-biphenylyl)-(3-nitro-4-chlorobenzyl)]-imidazole, 1-[α-(biphenylyl)-(3-nitrobenzyl)]-imidazole, 1-[bis(4-biphenylyl)-methyl]-imidazole, 1-[α-(4-biphenylyl)-benzyl]-1,2,4-triazole, 1-[α-(4-biphenylyl)-(2-chlorobenzyl)]-1,2,4-triazole, 1-[α-(4-biphenylyl)-(3-chlorobenzyl)]-1,2,4-triazole, 1-[α-(4-biphenylyl)-(4-chlorobenzyl)]-1,2,4-triazole, 1-[α-(4-biphenylyl)-(4-bromobenzyl)]-1,2,4-triazole, 1-[α-(4-biphenylyl)-(3-methylbenzyl)]-1,2,4-triazole, 1-[α-(4-biphenyl)-(4-tert.-butylbenzyl)]-1,2,4-triazole, 1-[α-(4-(4'-chlorobiphenylyl))-benzyl]-1,2,4-triazole, 1-[α-(4-(4'-chlorobiphenylyl))-(2-chlorobenzyl)]-1,2,4-triazole, 1-[α-(4-(2',4',6'-trichlorobiphenylyl))-benzyl]-1,2,4-triazole, 1-[α-(4-(3'-methylbiphenylyl))-benzyl]-1,2,4-triazole, 1-[α-(4-(3'-ethylbiphenylyl))-benzyl]-1,2,4-triazole, 1-[α-(4-biphenylyl)-(2,4-dichlorobenzyl)]-1,2,4-triazole, 1-[α-(4-biphenylyl)-(3-nitro-4-chlorobenzyl)]-1,2,4-triazole, 1-[α-(biphenylyl)-(3-nitrobenzyl)]-1,2,4-triazole and 1-[bis(4-biphenylyl)-methyl]-1,2,4-triazole.

The formula (III) provides a general definition of the halides also to be used as starting materials. In this formula, $R^1$ and $R^2$ are identical or different and preferably represent hydrogen, straight-chain or branched alkyl with 1 to 4 carbon atoms and, preferably, optionally substituted phenyl, preferred substituents being the radicals which have already been mentioned preferentially for X in connection with the starting materials of the formula (II). $R^3$ preferably represents hydrogen, straight-chain or branched alkyl with 1 to 4 carbon atoms as well as optionally substituted phenyl, phenylalkyl with 1 to 4 carbon atoms in the alkyl part, phenylcarbonyl and phenylcarbonylalkyl with 1 to 4 carbon atoms in the alkyl part, preferred substituents being the radicals which have already been mentioned preferentially for Y in connection with the starting materials of the formula (II). Hal preferably represents fluorine, chlorine, bromine or iodine.

The starting materials of the formula (III) are generally known compounds in organic chemistry or can be obtained in the generally known and customary manner. The following may be mentioned as examples: α-(4-biphenylyl)-benzyl chloride, ω-bromo-acetophenone, ω-chloro-acetophenone, ω-chloro-(4-fluoroacetophenone), ω-bromo-(4-methylacetophenone), ω-chloro-(2,4-dichloroacetophenone), ω-chloro-(4-bromoacetophenone), 4-fluorobenzyl-methyl bromide, 4-chlorobenzylmethyl bromide, 2,4-dichlorophenyl-methyl chloride, diphenylmethyl chloride, (2-chlorophenyl)-diphenyl-methyl chloride, 4-chlorophenylcarbonyl-ethyl chloride, 4-bromophenylcarbonylethyl chloride, 4-fluorophenylcarbonyl-ethyl bromide, 4-chlorophenylcarbonyl-ethyl bromide, ω-bromo-ω-methyl-(4-methylacetophenone) and (4-chlorophenyl)-(4-fluorophenyl)-methyl chloride.

In the formula (I), Z preferably represents the anion of an inorganic or organic acid. These anions preferably include the halide anions, i.e. fluoride, chloride, bromide and iodide, as well as nitrate, sulphate and phosphate anions, and also acetate, propionate, glycollate, lactate, malonate, succinate, maleate, fumarate, tartrate, citrate, benzoate, methylsulphonate, ethylsulphonate, p-toluenesulphonate, benzenesulphonate or salicylate anions.

Preferred possible diluents for the reaction according to the invention are polar organic solvents. These include, preferentially, nitriles, such as acetonitrile, sulphoxides, such as dimethylsulphoxide, formamides, such as dimethylformamide, ketones, such as acetone, ethers, such as diethyl ether and tetrahydrofurane, and chlorohydrocarbons, such as methyllene chloride and chloroform.

In the process according to the invention, the reaction temperatures can be varied within a substantial range. In general, the reaction is carried out at between about 0° and about 120° C., preferably at about 20° to 90° C., or at the boiling point of the particular solvent.

In carrying out the process according to the invention, equimolar amounts are preferably used. The compounds of the formula (I) are isolated in the customary manner.

The anion exchange optionally to be carried out, in accordance with the process of the invention, in general takes place in the known manner (compare German Offenlegungsschrift No. 2,504,114), by converting the α-(4-biphenylyl)-benzyl-azolium halides of the formula (I) into the corresponding azolium hydroxides, for example, by means of a base or of an anion exchange resin, and then reacting them with an appropriate acid.

The following may be mentioned as examples of particularly active representatives of the active compounds of the invention, in addition to the preparation examples and the examples in Table 1: 1-[α-(4-biphenylyl)-benzyl]-3-(4-biphenylyl)-imidazolium chloride and 1-[α(4- biphenylyl)-benzyl]-3-diphenylmethyl-imidazolium chloride.

The new compounds of the formula (I) exhibit strong antimicrobial actions. They show a broad spectrum of action in vitro, embracing dermatophytes, yeasts, moulds and biphase fungi as well as Gram-positive cocci. In contrast to other known azole antimycotics the compounds according to the invention show an almost complete sporicidal action on dermatophyte spores and mould spores.

It is to be emphasised that the antimicrobial action of the compounds according to the invention already manifests itself within 20 minutes after addition to the cultures of micro-organisms, in some cases even substantially earlier. This is substantially earlier than, for example, in the case of the known azole antimycotic, clotrimazole. This property, surprising for azole antimycotics, of the action commencing rapidly, opens up the possibility of employing the active compounds according to the invention for combating microorganisms, especially in the hygiene sector and in the industrial field. The following may be mentioned as examples of possible fields of application:

as a detergent additive for disinfecting underwear (underpants, stockings and vests) in the course of the washing process in washing machines;

as an additive to oral hygiene products, for example toothpastes and mouthwashes, to avoid microbially caused infections of the mucrosa of the mouth, to act as a prophylactic against infection;

as a preservative for cosmetics.

Good results are obtained, in particular, at use concentrations of about 0.5 to 1% or more by weight, of active compounds.

The compounds according to the invention can be incorporated in the usual formulations, such as solutions, emulsions, suspensions, powders, pastes and granules. These may be produced in known manner, for example by mixing the active compounds with extenders, that is to say, liquid or solid or liquefied gaseous diluents or carriers, optionally with the use of surface-active agents, that is to say, emulsifying agents and/or dispersing agents and/or foaming agents. In the case of the use of water as an extender, organic solvents can, for example, also be used as auxilliary solvents.

As liquid diluents or carriers, especially solvents, there are suitable in the main, aromatic hydrocarbons, such as xylene, toluene, benzene or alkyl-naphthalenes, chlorinated aromatic or chlorinated aliphatic hydrocarbons, such as chlorobenzenes, chlorthylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide and dimethylsulphoxide, as well as water.

By liquefied gaseous diluents or carriers are meant liquids which would be gaseous at normal temperatures and under normal pressure, for example aerosol propellants, such as dichlorodifluoromethane or trichlorofluoromethane.

As solid carriers there are preferably used ground natural minerals, such as kaolins, clays, talc, chalk, quartz, attapulgite, montmorillonite or diatomaceous earth, and ground synthetic minerals, such as highly dispersed silicic acid, alumina and silicates.

Preferred examples of emulsifying and foam-forming agents include nonionic and anionic emulsifiers, such as polyoxyethylene-fatty acid esters, polyoxyethylene-fatty alcohol ethers, for example alkylaryl polyglycol ethers, alkyl sulphonates, alkyl sulphates and aryl sulphonates as well as albumin hydrolysis products; and preferred examples of dispersing agents include lignin sulphite waste liquors and methylcellylose.

Where appropriate, the formulation can also contain a perfume or flavouring material.

The invention particularly provides an antimicrobial composition containing, as an active ingredient, a compound of the invention in admixture with a solid or liquefied gaseous diluent or carrier or in admixture with a liquid diluent or carrier containing a surface-active agent and/or a perfume or flavouring material.

The invention also includes a method of combatting micro-organisms which comprises applying to the micro-organisms or to a habitat thereof, a compound of the invention alone or in admixture with a diluent or carrier.

EXAMPLE A: Antimycotic in-vitro activity

The in-vitro test was carried out in the series dilution test with germ inocula containing an average of $5 \times 10^4$ germs/ml of substrate. Nervina nutrient solution served as the nutrient medium. The incubation temperatures were 28° C. for dermatophytes, yeasts and moulds and 37° C. for biphase fungi; the duration of incubation was 24–96 hours.

| Active compound | MIC values in γ/ml of nutrient medium in the case of | | | | |
| --- | --- | --- | --- | --- | --- |
|  | Trichoph. ment. | Cand. alb. | Penicil. com. | Asperg. niger. | Microsp. felin. |
| 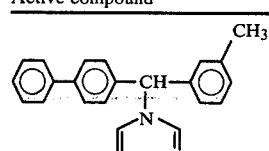 (known) | <1 | >64 | >64 | 64 | >64 |
| 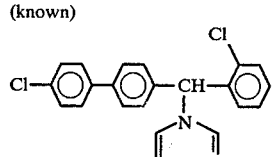 | <1 | >64 | 64 | >64 | 32 |

-continued

| Active compound | MIC values in γ/ml of nutrient medium in the case of | | | | |
| --- | --- | --- | --- | --- | --- |
| | Trichoph. ment. | Cand. alb. | Penicil. com. | Asperg. niger. | Microsp. felin. |
| (known) 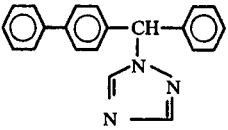 | <1 | >64 | >64 | >64 | >64 |
| (known) 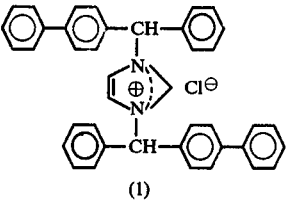 (1) | <1 | <1 | 8 | 1 | <8 |
| 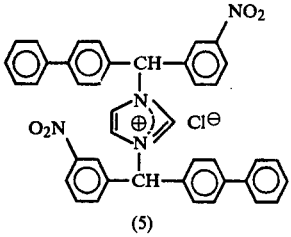 (5) | <1 | 4 | 4 | <1 | 8 |
| 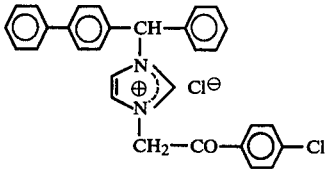 (6) | <1 | 8 | 8 | <1 | 2 |
| 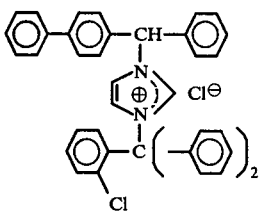 (3) | <1 | 4 | 8 | <1 | 4 |
| 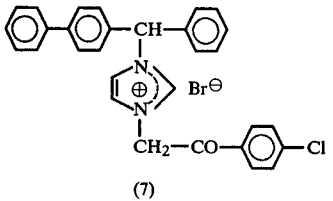 (7) | <1 | 8 | 8 | 4 | 32 |

Example B: Antibacterial in-vitro activity

The in-vitro tests were carried out by the plate test. In this, bacteria were cast with the agar at a concentration of $5 \times 10^3$/plate. The concentration in the plate which shows no colony formation is the MIC. Mueller Hinton bouillon served as the nutrient medium.

| Active compound | MIC values in the case of | | | |
|---|---|---|---|---|
| | Staph. albus | Staph. aureus | Strept. pyogenes | Strept. faecalis |
| 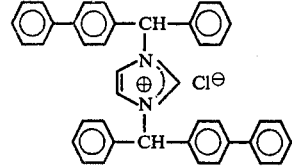 (1) | 8–32 | 8–32 | 8–32 | 8–32 |

Example C: Sporicidal action

In contrast to other azole antimycotics, the compounds according to the invention exhibit a sporicidal activity on dermatophyte spores and mould spores.

Test arrangement:

About $10^4$ spores of *Trichophyton mentagrophytes* or Trichophyton Quinckeanum or *Aspergillus fumigatus* are suspended per ml of NaCl solution and the particular active compound is added in concentrations of 1, 5, 10, 50 and 100 γ/ml of suspending solution. The spore suspension is incubated for 24, 48, 72, 96, 120 and 240 hours; after the stated incubation times 0.1 ml is withdrawn per concentration and per tube and smeared homogeneously over malt extract Petri dishes, and the number of spores still germinating after 48 hours' incubation time at 28° C. is counted in comparison to the untreated control.

At concentrations of 5γ/ml the compound from Example 1 shows an almost complete sporicidal action on the abovementioned fungal spores.

Example D: Kinetics of the action

The kinetics of the action are followed by means of continuous turbidimetric measurements.

The compound from Example 1, at concentrations of 5 and 10 γ/ml, shows, in the case of the test organism Candida albicans, an action commencing already about 5–10 minutes after addition of the preparation to the micro-organism cultures. The germs cease to grow and no further reproduction occurs.

Example E: Use as a detergent additive

4×4 cm pieces of fine tights were impregnated with aqueous germ suspensions of Candida albicans and Trichophyton mentagrophytes in such a way that $5 \times 10^3 - 1 \times 10^4$ germs were present per cm² of fabric.

The pieces of fabric were placed in beakers (a) in tapwater, (b) in 0.5% strength solutions of Example 1 and (c) in 1.0% strength solutions of Example 1, and stirred by means of a magnetic stirrer in the said solutions for 20, 60 and 120 minutes.

After the stated times, the pieces of fabric were taken out and dried for 1 hour at 30° C. in a vacuum drying cabinet.

The dried pieces of fabric were placed on Nervina agar plates and incubated for 48 hours at 28° C. We found:

(a) in the tapwater control: 1,000 germs per 4 cm² after 20 and 60 minutes, about 400 germs after 120 minutes;

(b) with 0.5% strength Example 1: about 100 germs per 4 cm² after 20 and 60 minutes, 10–20 germs after 120 minutes.

(c) with 1.0% strength Example 1: 5–10 germs after 20 and 60 minutes, 0 germs after 120 minutes.

Preparation Examples

EXAMPLE 1

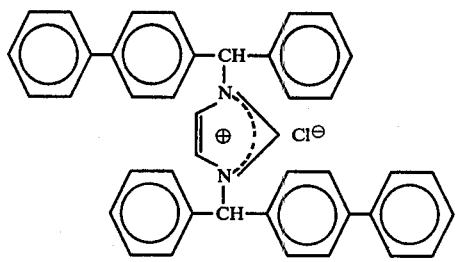

31 g (0.1 mol) of 1-[α-(4-biphenylyl)-benzyl]-imidazole and 27.9 g (0.1 mol) of α-biphenylyl-benzyl chloride are suspended in 200 ml of acetonitrile. The mixture is heated under reflux for 18 hours. The reaction mixture is then concentrated by distilling off the solvent and the residue, in 500 ml of toluene, is heated under reflux. The gel thereby formed is separated off and caused to crystallise by trituration with diisopropyl ether. 36 g (62% of theory) of 1,3-bis-[α-(-biphenylyl)-benzyl]-imidazolium chloride of melting point 150° C. (with decomposition) are obtained.

Starting material:

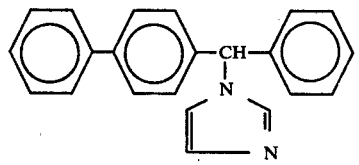

13.6 g (0.1 mol) of imidazole are dissolved in 150 ml of acetonitrile and 3.5 ml of thionyl chloride are added at 10° C. 13 g (0.05 mol) of 4-biphenyl-phenyl-carbinol are added to the solution of thionyl-bis-imidazole, thus obtained. After standing for 15 hours at room temperature, the solvent is removed by distilling off in vacuo. The residue is taken up in chloroform and the solution is washed with water. The organic phase is separated off, dried over sodium sulphate and filtered and the solvent is distilled off in vacuo. The oily residue is dissolved in ethyl acetate and freed from insoluble, resinous constituents by filtration. The solvent is again distilled off in vacuo and the residue is purified by recrystallisation from acetonitrile. 8.7 g (56% of theory) of 1-[α-(4-biphenylyl)-benzyl]-imidazole of melting point 142° C. are obtained.

Starting material:

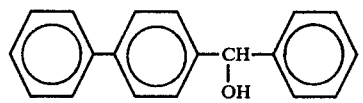

38.8 g (0.15 mol) of 4-phenyl-benzophenone are dissolved in 200 ml of ethanol and 3 g (0.075 mol) of sodium borohydride are added. After heating for 15 hours under relfux, the reaction mixture, when cold, is hydrolysed with water containing a small amount of hydrochloric acid. The solid thereby produced is purified by recrystallisation from ethanol. 36 g (89% of theory) of 4-biphenyl-phenylcarbinol of melting point 72°–73° C. are obtained.

EXAMPLE 2

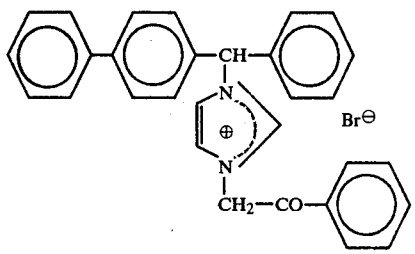

15.1 g (0.05 mol) of 1-[α-(4-biphenylyl)-benzyl]-imidazole and 10 g (0.05 mol) of ω-bromoacetophenone are suspended in 500 ml of acetonitrile. After stirring for 15 hours at room temperature, the resulting clear solution is concentrated to about 50 ml. The crystals which hereupon separate out are filtered off and dried. 21 g (82.5% of theory) of 1-[α-(4-biphenylyl)-benzyl]-3-phenacylimidazolium bromide of melting point 210° C. (with decomposition) are obtained.

EXAMPLE 3

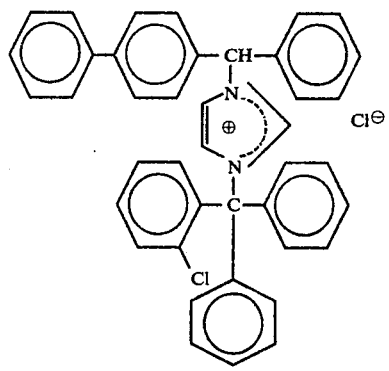

15.1 g (0.05 mol) of 1-[α-(4-biphenylyl)-benzyl]-imidazole and 15.2 g (0.05 mol) of 2-chlorophenyl-diphenylmethyl chloride are suspended in 400 ml of acetonitrile and the suspension is heated to 80° C. for 24 hours. It is then filtered and the filtrate is concentrated by distilling off the solvent. The residue crystallises after trituration with ether. 13 g (42% of theory) of 1-[α-(4-biphenylyl)-benzyl]-3-(2-chlorophenyl-diphenyl-methyl)-imidazolium chloride of melting point 140° C. (with decomposition) are obtained.

The compounds of Table 1 below are obtained analogously to Examples 1 to 3.

TABLE 1

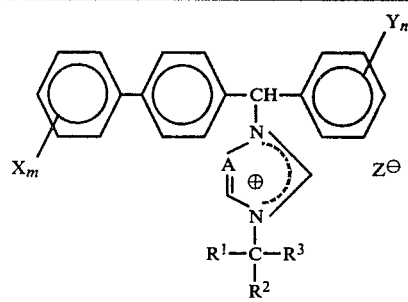

| Example No. | A | R$^1$ | R$^2$ | R$^3$ | X$_m$ | Y$_n$ | Z | Melting point (°C.) |
|---|---|---|---|---|---|---|---|---|
| 4 | CH | NO$_2$, Cl— (phenyl)— | H | —(phenyl)—(phenyl) | — | 4-Cl 3-NO$_2$ | Cl | 60 (decomposition) |
| 5 | CH | NO$_2$— (phenyl)— | H | —(phenyl)—(phenyl) | — | 3-NO$_2$ | Cl | 70 (decomposition) |
| 6 | CH | H | H | —CO—(phenyl)—Cl | — | — | Cl | 150 (decomposition) |
| 7 | CH | H | H | —CO—(phenyl)—Cl | — | — | Br | 170 (decomposition) |

TABLE 1-continued

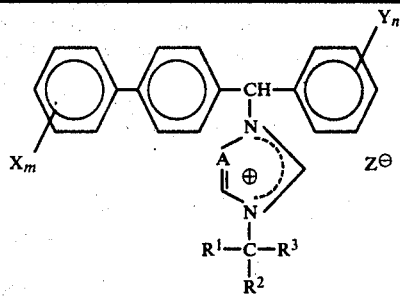

| Example No. | A | R¹ | R² | R³ | X_m | Y_n | Z | Melting point (°C.) |
|---|---|---|---|---|---|---|---|---|
| 8 | CH | 2,4-di-Cl-phenyl | H | biphenyl | — | 2,5-Cl₂ | Cl | 200 (decomposition) |
| 9 | CH | H | H | phenyl | — | — | Cl | viscous oil 150 |
| 10 | N | phenyl | H | biphenyl | — | — | Cl | 164 (decomposition) |
| 11 | CH | phenyl | H | biphenyl | — | — | NO₃ | 102 |
| 12 | CH | phenyl | H | biphenyl | — | — | SO₄ | 110 |
| 13 | CH | phenyl | H | biphenyl | — | — | PO₄ | 120 |
| 14 | CH | phenyl | H | biphenyl | — | — | Acetate | 86 |
| 15 | CH | phenyl | H | biphenyl | — | — | Tartrate | 72 |
| 16 | CH | phenyl | H | biphenyl | — | — | Citrate | 105 |
| 17 | CH | phenyl | H | phenyl | — | — | Cl | 152–156 (decomposition) |
| 18 | CH | C(CH₃)₃ | H | biphenyl | — | — | Cl | 170 |
| 19 | CH | phenyl | H | biphenyl | — | — | OH | 82 |

What is claimed is:

1. An α-(4-Biphenylyl)-benzylazolium salt of the formula $$\text{(I)}$$

in which

A represents the CH group or a N atom,

R¹ and R² are identical or different and each represents hydrogen, alkyl with 1 to 4 carbon atoms, unsubstituted phenyl or phenyl substituted by halogen, alkyl with 1 to 6 carbon atoms, halogenoalkyl with 1 to 4 carbon atoms alkoxy with 1 to 4 carbon atoms, alkylthio with 1 to 4 carbon atoms, nitro or cyano, R³ represents unsubstituted or substituted phenyl or biphenyl, phenylalkyl with 1 to 4 carbon atoms in the alkyl part, phenylcarbonyl or phenylcarbonylalkyl group with 1 to 4 carbon atoms in the alkyl part the substituents being fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano, X represents halogen, alkyl with 1 to 6 carbon atoms, halogenoalkyl with 1 to 4 carbon atoms and up to 5 halogen atoms, alkoxy with 1 to 4 carbon atoms, alkylthio with 1 to 4 carbon atoms, nitro or cyano, Y represents X or unsubstituted phenyl or phenyl substituted by halogen, alkyl with 1 to 6 carbon atoms, halogenoalkyl, alkoxy with 1 to 4 carbon atoms, alkylthio with 1 to 4 carbon atoms, nitro or cyano, m and n each represents 0 or an integer of from 1 to 5 and Z represents the anion of an inorganic or organic acid.

2. A compound of claim 1 wherein, in Formula (I),

X represents fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano Y represents fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro, cyano or a phenyl group, unsubstituted or substituted by one or more of fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano $R^1$ and $R^2$ individually represent hydrogen, straight or branched chain alkyl with 1 to 4 carbon atoms, or a phenyl group unsubstituted or substituted by one or more of fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano $R^3$ represents unsubstituted or substituted phenyl or biphenyl, or phenylcarbonyl radical, an unsubstituted or substituted phenylalkyl or phenylcarbonylalkyl radical with 1 to 4 carbon atoms in the alkyl part, the substituents being fluorine, chlorine, bromine, alkyl with 1 to 6 carbon atoms, halogenoalkyl with 1 to 4 carbon atoms and up to 5 halogen atoms, alkoxy with 1 to 4 carbon atoms, nitro or cyano m and n each represents 0, 1, 2 or 3, and Z represents a halide, nitrate, sulphate, phosphate, acetate, propionate, glycollate, lactate, malonate, succinate, maleate, fumarate, tartrate, citrate, benzoate, methyl sulphonate, ethylsulphonate, p-toluenesulphonate, benzenesulphonate or salicylate anion.

3. An antimicrobial composition containing an effective amount of a compound of claim 1 in admixture with a solid or liquefied gaseous diluent or carrier or in admixture with a liquid diluent or carrier containing a surface-active agent, a perfume or a flavouring.

4. A method of combatting micro-organisms which comprises applying to the micro-organisms or to a habitat thereof, an effective amount of a compound of claim 1 alone or in admixture with a diluent or carrier.

5. An antimicrobial composition of claim 3 containing at least 0.5% by weight of a compound of claim 1.

6. A method of claim 4 wherein there is applied at least 0.5% by weight of the active compound.

7. A compound of claim 1 having the formula

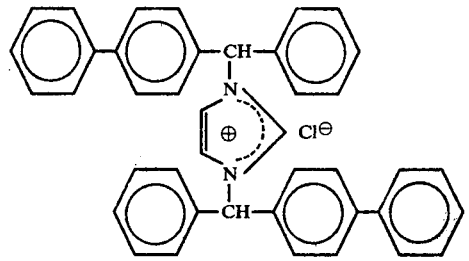

8. A compound of claim 1 having the formula

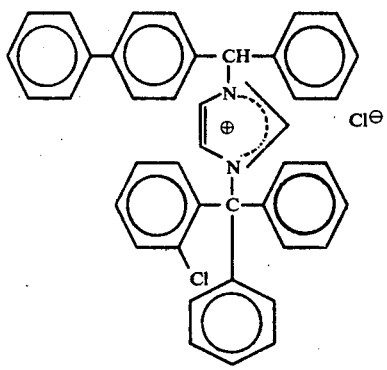

9. A compound of claim 1 having the formula

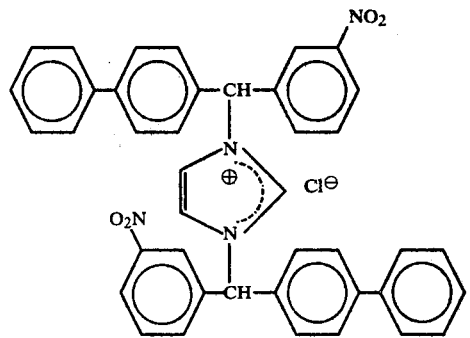

* * * * *